United States Patent [19]

Lussier et al.

[11] Patent Number: 5,254,592

[45] Date of Patent: Oct. 19, 1993

[54] MULTIPLY SUBSTITUTED ANILINES, PHENOLS AND PYRIDINES-IMMUNOMODULATING AGENTS

[75] Inventors: Barbara B. Lussier, Rochester, N.J.; Lee H. Latimer, Rochester, N.Y.; Carl R. Illig, Phoenixville, Pa.; William N. Washburn, Titusville, N.J.

[73] Assignee: Sterling Drug Inc., New York, N.Y.

[21] Appl. No.: 815,447

[22] Filed: Dec. 31, 1991

[51] Int. Cl.$^5$ .................. A61K 31/165; C07C 233/65
[52] U.S. Cl. ...................................... 514/617; 514/349; 514/563; 514/616; 514/619; 514/622; 546/297; 562/455; 564/155; 564/157; 564/158; 564/169; 564/171
[58] Field of Search ............... 564/168, 171, 163, 165, 564/167; 514/617, 619, 618

[56] References Cited

U.S. PATENT DOCUMENTS

| | | | |
|---|---|---|---|
| 2,756,149 | 7/1956 | Saunder et al. | 430/515 |
| 2,772,163 | 11/1956 | Tong | 430/545 |
| 4,263,039 | 4/1981 | Noguchi et al. | 564/171 |
| 4,471,045 | 9/1984 | Bodem et al. | 430/218 |

*Primary Examiner*—Glennon H. Hollrah
*Assistant Examiner*—Shailendra Kumar
*Attorney, Agent, or Firm*—Imre Balogh; Arthur Rosenstein

[57] ABSTRACT

In accordance with the present invention, certain multiply substituted anilines, phenols and pyridines and pharmaceutically acceptable salts thereof are provided which mimic IL-1 activity by inducing IL-2 synthesis and subsequent IL-2 receptor expression. Specifically, the invention provides compounds of Formula I and acid addition salts thereof:

FORMULA I

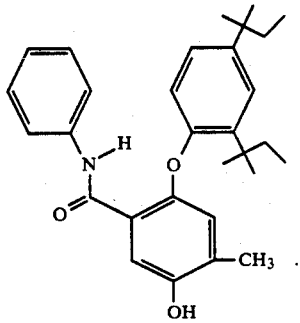

2 Claims, No Drawings

MULTIPLY SUBSTITUTED ANILINES, PHENOLS AND PYRIDINES-IMMUNOMODULATING AGENTS

BACKGROUND OF THE INVENTION

1. Field of the Invention

The present invention relates to multiply substituted anilines, phenols and pyridines, methods for their preparations and, to their use as immunomodulating agents. More specifically, the present invention relates to multiply substituted anilines, phenols and pyridines, having interleukin (hereinafter IL-1) activity, which can be used as a stimulant of the immune functions.

2. Reported Developments

IL-1 is a 17 kD polypeptide hormone which induces a wide range of biological effects by binding IL-1 to a specific receptor protein on responsive cells. Some of the activities of IL-1 include: induction of IL-2 secretion from T cells, induction of fibroblasts to secrete PGE, stimulation of osteoclasts to resorb bone, triggering the appearance of CSF receptors on stem cell progenitors, increasing synthesis of CSF's, activation of T and B cells, induction of cartilage destruction in joints, elevation of collagenase levels in synovial fluid and action as an endogenous pyrogen.

Because of the multiple activities of IL-1, a variety of uses for compounds influencing these responses have been envisioned. An IL-1 agonist or mimetic would have therapeutic applications as an immunostimulant, an anticancer agent or in inducing haemopoesis.

IL-1 has been produced in the prior art by inducing secretion thereof by normal macrophages/monocytes of peripheral blood by means of application of an inducing agent of bacterial origin. IL-1 has also been produced by culturing a human leukemic cell line of haematopoietic origin by means of application of phorboles as inducing agents. Another approach to provide for IL-1 activity is disclosed in U.S. Pat. No. 4,762,914 which teaches the production of truncated protein of IL-1 made by a genetic engineering procedure. The so obtained biologically active human IL-1 protein is said to be useful to induce the production of IL-2 by activated T-cells. Still another approach to provide IL-1 activity is disclosed in U.S. Pat. No. 4,774,320 which concerns the preparation and use of the following peptide that mimics human IL-1 activity:

Val-Gln-Gly-Glu-Glu-Ser-Asn-Asp-Lys-X where
X=cysteine (Cys), OH, $NH_2$, benzyl ester or an alkyl ester group having a number of carbon atoms from 1 to 7.

IL-2, also known as T cell growth factor, has been found to influence cell-mediated immune responses in mammals, such as: enhancement of thymocyte mitogenesis; production of cytotoxic T lymphocytes; promotion of proliferation of antigen specific killer T cell lines; and promotion of antierythrocyte placque forming cell responses.

Disruptions of the immunodefense system can be ascribed to the insufficient presence of IL-2 in the mammalian body, as a result of the lack of cells that produce IL-2, inadequate IL-2 production, or insufficient formation of IL-2 eptors (U.S. Pat. No. 4,752,573). In light of these findings by the prior art, IL-2 appears to be useful in promoting humoral and cellular immune responses and in restoring an immune deficient state to a normal immune state. Accordingly, IL-2 is indicated for medical immunotherapy against immunological disorders, including neoplastic diseases, bacterial or viral infections, immune deficient disorders and autoimmune diseases.

IL-2 has been produced in the prior art by stimulating mouse, rat or human lymphocytes with a mitogen (Gillis, S. et al., Nature, 268, 154-156, (1977), Farrat, J. et al., J. Immunol., 121, 1353-1360, (1978), Gillis, S. et al., J. Immunol., 120, 2027-2033, (1978)) or by stimulating human peripheral blood mononuclear lymphocytes with a mitogen (Gillis, S. et al., J. Immuno., 124, 1954-1962, (1980)). Gillis et al. reported the preparation of murine IL-2 from murine T cell lymphoma cell line (Gillis, S. et al. J. Immunol., 125, 2570-2578 (1980)) and preparation of human IL-2 from a human leukemia cell line (Gillis, S. et al., J. Exp. Med., 152, 1709-1719, (1980)).

Other methods of preparations, compositions and use thereof are illustrated by the following references.

U.S. Pat. No. 4,404,280 discloses a process for producing murine IL-2 from malignant neoplastic cells in vitro in a protein-containing medium. The process includes the utilization of IL-1 as a co-stimulant to induce IL-2 production.

U.S. Pat. No. 4,406,830 relates inter alia, to a process for producing a serum-free and mitogen-free IL-2 in vitro by adding glycoprotein to a serum-free and mitogen-free IL-1 preparation.

U.S. Pat. No. 4,738,927 discloses a method of producing IL-2 by isolating a gene which possesses IL-2 activity, connecting said gene with a vector DNA which is capable of replicating in a procaryotic or eucaryotic cell at a position down-stream of a promoter gene in the vector to obtain a recombinant DNA, with which the cell is transformed to produce IL-2.

U.S. Pat. No. 4,752,573 relates to the use of pterins to increase the activity of lymphokines and other cell growth factors, including IL-2.

U.S. Pat. No. 4,780,313 discloses a method for immunostimulating a warm-blooded animal by administering to said animal a substance having IL-2 activity, such as a recombinant non-glycosylated human IL-2, in combination with muramyldipeptide.

U.S. Pat. No. 4,789,658 relates to an immunoprophylactic and immunotherapeutic composition comprising grade E human IL-2 of human T-lymphocyte origin.

The utility of IL-2 to supplement immune responses and thus the need for IL-2 mediators to proliferate other effector cells, such as T-helper and suppressor cells, cytotoxic T-cells and natural killer cells (hereinafter NKC's) to promote cell-mediated immunity, is apparent from the above-described references.

It should also be noted that IL-1, or a biologically active compound that mimics IL-1 activity, plays a very important role as an immunostimulating agent by inducing IL-2 synthesis and subsequent IL-2 receptor expression.

We have now discovered a class of organic compounds which promote cell-mediated immunity based on their capability to elevate IL-2 and granulocyte macrophage colony stimulating factor (hereinafter GM-CSF) levels in vitro and thus proliferate effector cells, such as cytotoxic T-cells lines and other subpopulations of T-cells.

SUMMARY OF THE INVENTION

In accordance with the present invention, certain multiply substituted anilines, phenols and pyridines and pharmaceutically acceptable salts thereof are provided which mimic IL-1 activity by inducing IL-2 synthesis and subsequent IL-2 receptor expression. Specifically, the invention provides compounds of Formula I and acid addition salts thereof:

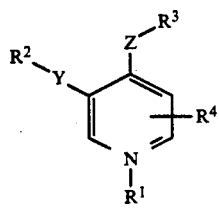

FORMULA I wherein
Y is

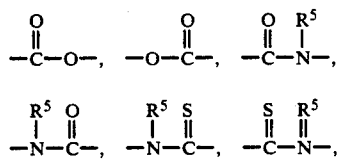

$NHSO_2$ or $SO_2NH$ where $R^5$ is H;

Z is —O—, —NH—, —NR—, —S—, or other heteroatoms capable of hydrogen bonding with $R^5$ to give a preferred conformation;
R is alkyl;
X is C or N;
$R^1$ is —OH, hydroxyalkyl, —$NH_2$, aminoalkyl, carboxy, glycylamino, alanylamino, phenylalanylamino, amido, amidino or a lone pair of electrons, with the proviso that when X is N, $R^1$ is a lone pair of electrons;
$R^2$ is H, alkyl, cycloalkyl, aralkyl, substituted or unsubstituted aryl, or a substituted or unsubstituted nitrogen heterocyclic group having 4 to 5 nuclear carbon atoms;
$R^4$ is H, alkyl, cycloalkyl, halo or hydroxyalkyl with the proviso that when $R^1$ is, —OH, —$NH_2$ or —$NHCH_3$, $R^4$ cannot be H; and
$R^3$ is a lipophilic moiety.

DETAILED DESCRIPTION OF THE INVENTION

As employed above and throughout the specification the following terms, unless otherwise indicated, shall be understood to have the following meaning:

The "alkyl" group per se and in alkoxy means a saturated or unsaturated aliphatic hydrocarbon which may be either straight- or branched-chained containing from one to about 10 carbon atoms. Lower alkyl is preferred having from one to six carbon atoms.

The "cycloalkyl" groups may be mono or polycyclic and contain 3 to 16 carbon atoms and include cyclopropyl, cyclobutyl, cyclopentyl, cyclohexyl, cycloheptyl and cyclooctyl.

"Aryl" contains from 6 to 10 carbon atoms and include phenyl, tolyl, xylyl, naphthyl and the like.

"Substituted aryl" means an aryl group substituted by one or more lower alkyl, lower alkoxy, amino, lower alkyl amino, lower alkyl mercapto, hydroxy, hydroxy lower alkyl, acetoxy, benzyloxy, phenoxy, carboxy, carboalkoxy, halo, amido, halosulfonyl, lower alkyl sulfinyl or lower alkyl sulfonyl.

"Aralkyl" means an aromatic hydrocarbon radical containing from 7 to about 16 carbon atoms and include benzyl, phenethyl, naphthylmethyl and the like.

The "heterocyclic" groups may be mono or polycyclic and include such groups as pyridyl, pyrimidinyl, quinolyl, quinolinyl, piperidyl, pyrrolyl, morpholinyl, thiomorpholinyl, thiophenyl, furyl, furfuryl, thienyl, imidazolyl, benzimidazolyl, and the like. These groups may carry substitutents such as alkyl, alkenyl, alkynyl, hydroxy, thio, amino, alkylamino, dialkylamino, alkoxy, alkylthio and halo.

"Lipophilic" means a moiety having from about 1 to about 22 carbon atoms in the entire group and includes substituted or unsubstituted, straight-or branched-chain alkyl, cycloalkyl, neopentyl, nonyl, isononyl, alkyladamantyl, 2,4-dimethylbenzyl, substituted or unsubstituted phenyl, such as 2,4-bis(1,1-dimethylpropyl)phenyl or 2-naphthyl.

When $R^2$ is substituted aryl it can have up to five of the lipophilic substituents described under "lipophilic" above or any combination of members of said lipophilic group with a polar substituent, such as cyano, amino, hydrazino, acetylhydrazino, arylazo, fluorosulfonyl or carboxamido.

"Halogen" means Cl, F, I or Br.

Preferred compounds of this invention are aryloxy anilides and aryloxyphenols having the structure of Formula II:

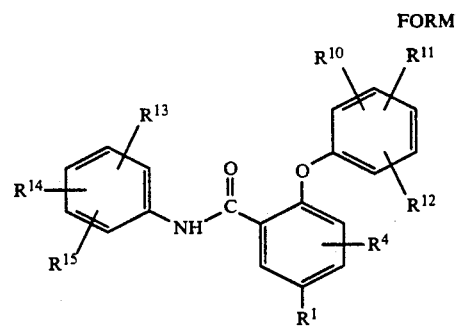

FORMULA II wherein
$R^4$ is alkyl, cycloalkyl, halo or hydroxyalkyl;
$R^1$ is —$NH_2$, or —OH;
$R^{10}$, $R^{11}$ and $R^{12}$ are independently H or a lipophilic group, or any two of $R^{10}$, $R^{11}$ and $R^{12}$ can be taken together with the phenyl nucleus to which they are attached to form a β-naphthyl group; and
$R^{13}$, $R^{14}$ and $R^{15}$ are independently H, a lipophilic group or a polar group.

Other preferred compounds are: N-(1,1-dimethylethyl)-2-(2,4-bis(1,1-dimethylpropyl)phenoxy)-5-hydroxy-4-methylbenzamide, 5-(2,4-bis(1,1-dimethylpropyl)phenoxy)-2,3-dihydro-6-benzofuranilide and 2-(2,4-bis(1,1-dimethylpropyl)phenoxy)-5-hydroxy-6-(3-hydroxypropyl)benzanilide.

Compounds of the present invention may be prepared by the following Schemes:

SCHEME 1

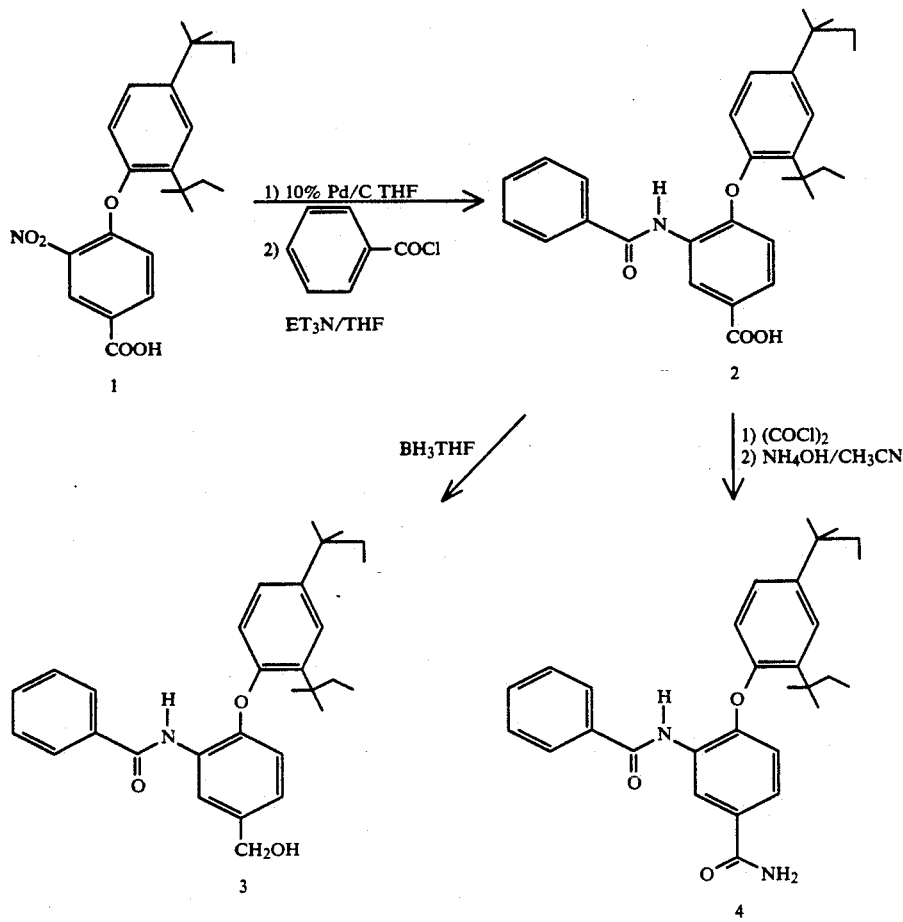

In Scheme 1, compounds were derived from 3-nitro-4-bis(1,1-dimethylpropyl) phenoxy-benzoic acid, 1. As shown, 1 was catalytically reduced with 10% palladium on carbon catalyst in THF and then reacted with benzoyl chloride in THF to yield the carboxylic derivative 2. Reduction of the carboxylic acid with borane-tetrahydrofuran complex provided a 50% yield of benzyl alcohol 3. Formation of the acid chloride of 2 with oxalyl chloride and subsequent reaction with ammonium hydroxide in acetonitrile proceeded cleanly to an 85% yield of the unsubstituted amide, 4.

Compounds shown in Table 1 can be made using Scheme 1 or schemes analogous to Scheme 1.

TABLE 1

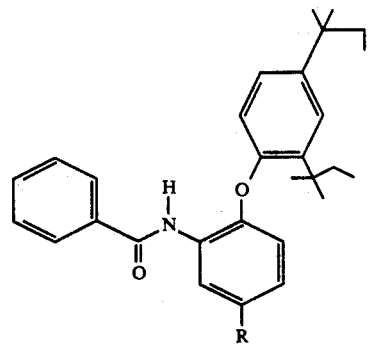

| COMPOUND NO. | R |
|---|---|
| 2 | COOH |
| 3 | CH$_2$OH |
| 4 | CONH$_2$ |
| 5 | NHCOCH(NH$_2$)CH$_2$Phenyl |
| 6 | NHCO(CH$_2$)COOH |
| 7 | NHCOCH(CH$_3$)NH$_2$ |
| 8 | NHCOCH$_2$NH$_2$ |
| 9 | NHCOCH$_3$ |
| 10 | NHCOPhenyl |
| 11 | NHCH(CH$_3$)$_2$ |

Scheme 2 illustrates the preparation of compounds according to Formula I wherein $R^4$ is other than hydrogen.

SCHEME 2

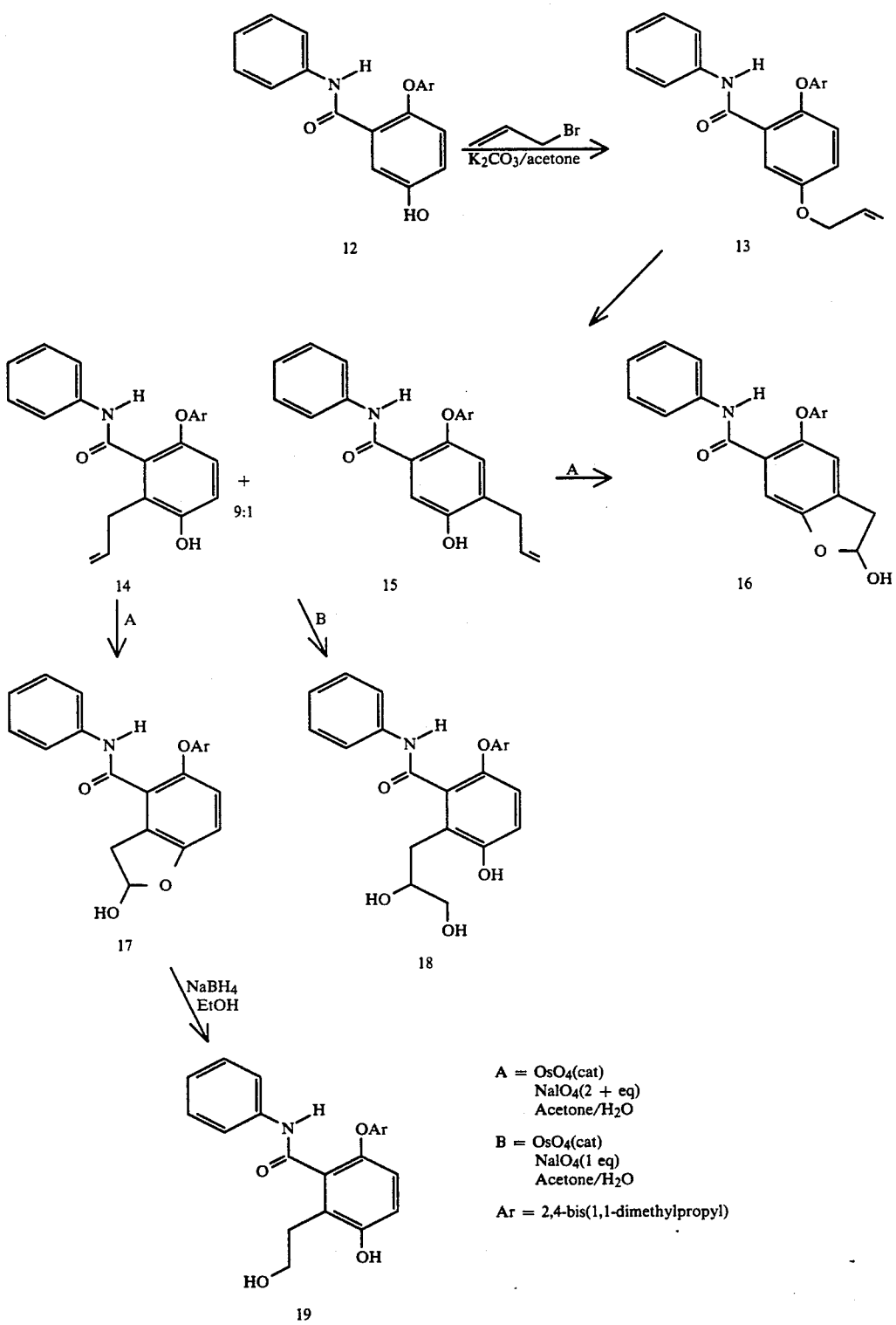

A = OsO₄(cat)
    NaIO₄(2 + eq)
    Acetone/H₂O

B = OsO₄(cat)
    NaIO₄(1 eq)
    Acetone/H₂O

Ar = 2,4-bis(1,1-dimethylpropyl)

In Scheme 2, phenol, 12, was refluxed for 3 hours with allyl bromide, potassium carbonate and acetone to obtain the allyl ether derivative, 13 (yield: 98%). A Claisen rearrangement with N,N-diethylamine yielded a 9:1 mixture of the 6-allyl, 14, and 4-allyl, 15, derivatives which were then separated chromatographically. The 4-allyl derivative was then treated with two equivalents of sodium periodate and a catalytic amount of osmium tetroxide in acetone/water to obtain the cyclic ether derivative, 16. The 6-allyl derivative, subjected to one equivalent sodium periodate and catalytic osmium tetroxide, yielded the glycol, 18. Whereas cyclic ether, 17, was obtained similarly to compound 16 using two equivalents of sodium periodate and a catalytic amount of osmium tetroxide in acetone/water. Reacting compound 17 with sodium borohydride in ethanol resulted in 6-hydroxypropyl compound 19.

Compounds 14, 15, 18 and 19, made according to Scheme 2 are shown in Table 2. Compounds 16 and 17, also shown in Table 2, were synthesized as follows:

2-(2,4-Bis(1,1-dimethylpropyl)phenoxy)-5-methoxybenzylalcohol was treated with n-butyllithium in THF and quenched with iodomethane to yield a 1:1 mixture of 4-methyl and 6-methyl material which was separated by chromatography. Swern oxidation of the benzyl alcohol, followed by treatment with oxalyl chloride and then t-butylamine, provided the desired 5-methoxy amides which were then cleaved with BBr3 to yield the desired 4-methyl and 6-methyl derivatives.

TABLE 2

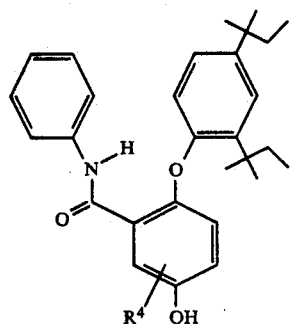

| COMPOUND NO. | R |
|---|---|
| 14 | 6-CH2CHCH2 |
| 15 | 4-CH2CHCH2 |
| 16 | 4-CH3 |
| 17 | 6-CH3 |
| 18 | 6-CH2CH(OH)CH2OH |
| 19 | 6-CH2CH2OH | which was catalytically reduced with Pd/C in ethanol (90%) and finally reacted with benzoyl chloride to yield the pyridinium compound 25.

The following preparative examples will further illustrate the invention.

EXAMPLE 1

3-Benzamido-4-(2,4-bis(1,1-dimethylpropyl)phenoxy)-pyridine

A. A solution of 2,4-bis(1,1-dimethylpropyl)phenol (9.23 g, 0.039 mol) in dry tetrahydrofuran (30 mL) was stirred at room temperature under nitrogen atmosphere. Sodium hydride (1.14 g of 80% dispersion, 0.04 mol) in dry tetrahydrofuran (10 mL) was added and the mixture stirred for 30 minutes to give a clear, green solution. 4-Chloro-3-nitropyridine (5.0 g, 0.032 mol) was added and the mixture heated to 50° C. for 4 hours. The mixture was cooled and submitted to aqueous, acidic work-up. The crude product was purified by chromatogaphy on silica gel with dichloromethane eluent to give the product 3-nitro-4-(2,4-bis(1,1-dimethylpropyl)phenoxy)-pyridine in 65% yield. Analyses by proton NMR and mass spectroscopy were consistent with the proposed structure.

B. 3-Nitro-4-(2,4-bis(1,1-dimethylpropyl)phenoxy)-pyridine (6.0 g, 0.017 mol) was dissolved in ethanol (50 mL) and catalytically reduced by hydrogen with Pd/C catalyst at room temperature for 2 hours. The mixture was filtered through filter-cel and the ethanol removed in vacuo to yield the pure product 3-amino-4-(2,4-bis(1,1-dimethylpropyl)phenoxy)-pyridine in 98% recovered yield. Mass spectral and NMR data were consistent with the proposed structure.

C. 3-Amino-4-(2,4-bis(1,1-dimethylpropyl)phenoxy)-pyridine (3.0 g, 9.2 mmol) was dissolved in tetrahydrofuran (10 mL) and cooled to 10° C. Benzoyl chloride (1.3 g, 9.2 mmol) in tetrahydrofuran (10 mL) was added dropwise. Triethylamine (0.93 g, 9.2 mmol) in tetrahydrofuran (5 mL) was added and the mixture warmed to room temperature and stirred for 2 hours. The mixture was submitted to standard aqueous acidic workup. The crude solid obtained was recrystallized from acetonitrile to yield the title product as a white solid in 80%

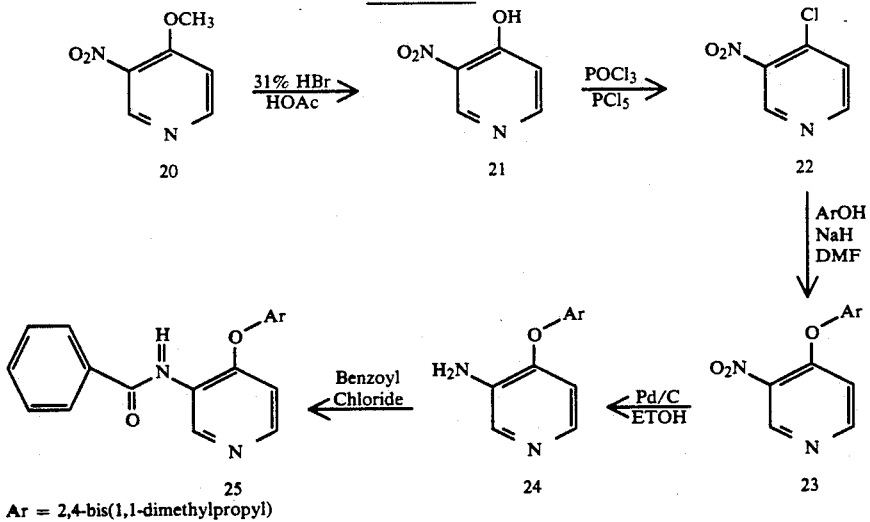

Ar = 2,4-bis(1,1-dimethylpropyl)

Scheme 3 illustrates the preparation of pyridinium compounds. 4-methoxy-3-nitropyridine 20 was deprotected with 31% HBr in acetic acid to provide a 91% yield of phenol, 21. Treatment of compound 21 with POCl3 and PCl5 at 125° C. for 3 hours yielded 4-chloro-5-nitropyridine, 22 in 73% yield. Further treatment with 2,4-bis(1,1-dimethylpropyl)phenol and NaH/DMF resulted in a 50% yield of aryl ether 23 yield, m.p. 253° C. Mass spectral and NMR data were consistent with the proposed structure.

EXAMPLE 2

N-tert-butyl 2-(2,4-bis(1,1-dimethylpropyl)phenoxy)-5-hydroxy-4-methyl benzamide.

A. To a solution of 5.04 g (13 mmol) of 2-(2,4-bis(1,1-dimethylpropyl)phenoxy)-5-methoxybenzoic acid in 15 ml of dry THF at 0° C. was added 15 ml of a 1M solution of borane-THF over a period of 15 min. The solution was stirred for 4 hrs while allowing it to slowly reach room temperature. The reaction mixture was carefully quenched with methanol until gas evolution ceased and then the solvents were removed at reduced pressure. The white solid residue was treated with 100 ml of 3N HCl and extracted with ethyl acetate. The ethyl acetate was washed with saturated aqueous NaHCO$_3$, dried over Na$_2$SO$_4$, and the ethyl acetate removed to yield 4.28 g of a clear, colorless compound, 2-(2,4-bis(1,1-dimethylpropyl)phenoxy-5-methoxy benzyl alcohol.

B. To a solution of 2.05 g (5.5 mmol) 2-(2,4-bis(1,1-dimethylpropyl)phenoxy)-5-methoxy benzyl alcohol in 10 ml of THF cooled to 0° C. was added 12 ml (19.2 mmol, 3.5 eq) in 1.6N n-BuLi in hexanes. The cooling bath was removed and the yellow solution brought to room temperature where it turned red over a period of 30 min. The solution was cooled to 0° C. and treated with 2 ml of iodomethane and allowed to warm to room temperature over 1 hr. The reaction was poured into 50 mol of 3N HCl and extracted with ethyl acetate. The organics were washed with water, dried with Na$_2$SO$_4$ and the solvent removed to yield the crude methylated alcohol. Flash chromatography with 1:1 CH$_2$Cl$_2$ and pentane yielded 0.45 g of the faster running 6-isomer and 0.5 g of the desired product 4-methyl-5-methoxy-2-(2,4-bis(1,1-dimethylpropyl)phenoxy benzyl alcohol, as well as 0.4 g of a mixture. The products were oils.

C. A solution of 0.5 g of 4-methyl-5-methoxy-2-(2,4-bis(1,1-dimethylpropyl)phenoxy benzyl alcohol in 10 ml of acetone was treated at room temperature with 2.5 ml of 1M Jones Reagent added dropwise until the red color persisted. After 6 hrs the reaction was worked up by dilution with water and extraction with ether. The organics were dried with Na$_2$SO$_4$ and solvents removed at reduced pressure to yield crude aldehyde. This material was recycled as above and stirred for 24 hrs. After dilution with water the mixture was extracted with ethyl acetate. The organics were washed with saturated aqueous NaHCO$_3$ solution. The aqueous NaHCO$_3$ solution was acidified and extracted with ethyl acetate. The organics were dried with Na$_2$SO$_4$ and the solvent removed at reduced pressure to yield the crude acid, which gave a solid from acetone and methanol and which was used without purification.

To a solution of the acid in 5 ml of toluene was added 0.3 ml of oxalyl chloride and one drop of DMF. After 1 hr the volatiles were removed at reduced pressure, 10 ml of toluene were added and removed at reduced pressure to yield the crude acid chloride which was used immediately by dissolving it in 5 ml of THF and adding 0.5 ml of tert-butyl amine. After stirring for 16 hr the solution was poured into ethyl acetate. This solution was washed with NaHCO$_3$ solution, dried with Na$_2$SO$_4$ and the solvents removed at reduced pressure. The crude methoxy amide was purified by chromatography to yield 0.26 g.

To a solution of 0.26 g of the methoxy amide at −78° C. in 1 ml of CH$_2$Cl$_2$ was added 1.5 ml (3 eq) of 1M boron tribromide in CH$_2$Cl$_2$ and the cooling bath removed. After 16 hrs the solution was poured into 50 ml of 3N HCl which was extracted with ethyl acetate. The organics were washed with water, saturated aqueous NaHCO$_3$ solution, dried with Na$_2$SO$_4$, and the solvents removed at reduced pressure. Crystallization of the crude hydroxy acid yielded 0.15 g of desired product N-tert-butyl 2-(2,4-bis(1,1-dimethylpropyl)phenoxy)-5-hydroxy-4-methyl benzamide, m.p. 223–225 (dec). from pentane.

EXAMPLE 3

4-Allyl-2-(2,4-bis(1,1-dimethylpropyl)phenoxy)-5-hydroxybenzanilide

A. To 4.77 g (10.7 mmol) of 2-(2,4-bis(1,1-dimethylpropyl)phenoxy-5-hydroxybenzanilide in 160 ml of reagent grade acetone was added 1.06 mL (12.3 mmol) of allyl bromide and 5.18 g (37.5 mmol) of anhydrous granular potassium carbonate and the mixture heated to reflux for 18 hrs. The mixture was concentrated to a thick slurry in vacuo, 150 mL of diethyl ether added and filtered through a pad of Celite. Concentration of the filtrate afforded 5.4 g of a colorless oil. Flash chromatography on 200 g of silica (5 cm column eluted with 10% ethyl acetate:hexanes) afforded 5.12 g (98%) of the pure allyl ether as a colorless syrup.

B. The allyl ether (5.12 g, 10.5 mmol) in 18.0 mL of N,N-diethylaniline was heated to a gentle reflux for 5 hrs under an argon atmosphere. The mixture was cooled, poured into 250 mL of 1M HCl and extracted with diethyl ether (2×100 mL). The combined extracts were washed with 1M HCl (2×100 mL), brine (100 mL) and dried over Na$_2$SO$_4$. Concentration of the solution in vacuo gave 5.12 g (100%) of a hard white foam (approximate 9:1 mixture of regioisomers by 'H-NMR). Flash chromatography on 200 g silica (5 cm column) eluting with 4% ethyl acetate:dichloromethane afforded 4.25 g (83%) of the major 6-allyl Claisen rearrangement product as a white foam. Elution with 10% ethyl acetate:dichloromethane afforded 0.54 g (11%) of the minor 4-allyl product, 4-allyl-2-(2,4-bis(1,1-dimethylpropyl)phenoxy-5-hydroxybenzanilide as a white foam.

EXAMPLE 4

2-(2,4-Bis(1,1-dimethylpropyl)phenoxy)-5-hydroxy-6-(2-hydroxyethyl) benzanilide

A. To 1.40 g (2.88 mmol) of the 4-allyl derivative product made in Example 3, in 60 mL of acetone:water (2:1) at 25° C. was dissolved 0.678 g (3.17 mmol) of sodium periodate followed by 1.46 mL (0.115 mmol) of 0.079M aqueous osmium tetroxide solution. After 1.5 hrs, and additional 0.678 g (3.17 mmol) of sodium periodate was added. After 2.5 hrs, the mixture was poured into 200 mL of diethyl ether, the organic layer washed with water (2×100 mL) and brine (100 mL), and dried over Na$_2$SO$_4$. Concentration of the solution afforded 1.39 g of a green foam. Flash chromatography on 90 g of silica (4 cm column, packed and eluted with 0.5% methanol:dichloromethane) afforded 1.23 g (88%) of pure product, 5-(2,4-bis(1,1-bis(dimethylpropyl)-phenoxy-2-hydroxy-4-benzofuranilide, as a light green foam.

B. To 205 mg (0.357 mmol) of unpurified benzofuranilide (prepared separately from above, 85% pure by 'H-NMR) in 6.0 mL of absolute ethanol at 25° C. was added 55.6 mg (1.47 mmol) of sodium borohydride. After 40 min, 12 mL of 1M HCl was added slowly, the mixture concentrated in vacuo and the residue extracted with 80 mL of diethyl ether. The extract was washed with brine, dried over $Na_2SO_4$ and concentrated to an off-white solid. Recrystallization from dichloromethane-hexanes afforded 110 mg (63%) of the pure alcohol 2-(2,4-bis(1,1-dimethylpropyl)phenoxy)-5-hydroxy-6-(2-hydroxyethyl)benzanilide as a white solid. Flash chromatography of the mother liquors on 15 g of silica (2 cm column eluting with 10% ethyl acetate:dichloromethane) afforded an additional 13.0 mg (7%) of the title product as a colorless glass.

The biological profile of the compounds of the present invention includes the following characteristics:
(a) Induction of secretion of IL-2 by murine EL-4 cells at concentrations as low as $4 \times 10^{-8}$M;
(b) Induction of IL-2 and granulocytes macrophage colony stimulating factor (GM-CSF) gene expression in EL-4 cells;
(c) Production of IL-3 and IL-4;
(d) Lack of binding IL-1, IL-2 or IL-4 receptors; neither agonists or antagonists to these lymphokines;
(e) Induction of proliferation of human thymocytes;
(f) Induction of proliferation of human T-cells and B-cells and murine T-cells;
(g) No indication of toxicity when administered IP, PO or IV; and
(h) Enhancement of human mixed lymphocyte reaction in a dose-dependent manner.

Based on these findings, the compounds of the present invention are useful for prophylaxis and therapy of immunological diseases. According to the kind of diseases, to the condition of the patients and to the immune state, the physician will determine the amount of the drug to be administered, the frequency of administration, routes of administration and vehicles containing the compounds to be administered.

The compounds of this invention can be normally administered parenterally, in the prophylaxis and treatment of immunological disorders. The compounds of this invention, or salts thereof, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents.

For parenteral administration, solutions or suspensions of these compounds in aqueous alcoholic media or in sesame or peanut oil or aqueous solutions of the soluble pharmaceutically acceptable salts described herein can be employed. Solutions of the salts of these compounds are especially suited for intramuscular and subcutaneous injection purposes. The aqueous compositions, including solutions of the salts dissolved in pure distilled water are also useful for intravenous injection purposes, provided that their pH is properly adjusted, suitably buffered, made isotonic with sufficient saline or glucose and sterilized by heating or by microfiltration. Certain compositions useful for intravenous injection or infusion may be prepared using the solid form of the active compound of the present invention. The solid compound may be suspended in propylene glycol, or a polyethylene glycol ether such as PEG 200, using a sonicator and the resulting mixture combined with aqueous media.

The dosage regimen in carrying out the methods of this invention is that which insures maximum therapeutic response until improvement is obtained and thereafter the minimum effective level which gives relief. It should be borne in mind that selecting the appropriate dosage in any specific case, consideration must be given to the patient's weight, general health, age and other factors which may influence response to the drug. The drug may be administered as frequently as is necessary to achieve and sustain the desired therapeutic response.

The present invention is also useful as an injectable dosage form which may be administered in an emergency to a patient. Such treatment may be followed by intravenous infusion of the active compound and the amount of compound infused into such patient should be effective to achieve and maintain the desired therapeutic response.

The following test results illustrate the beneficial effects of compounds of the present invention.

IL-1 BIOASSAY

EL-4 6.1 cells (murine T-cells) were first treated with mitomycin C to inhibit their proliferation. After washing the cells free of mitomycin C, the test compound ($10^{-5}$M) or the IL-1 standard ($3 \times 10^{-11}$M) was incubated with $2 \times 10^5$ EL-4 6.1 cells for 24 hours to allow gene expression and IL-2 synthesis. To quantify IL-2 production, CTLL-2 cells (IL-2 hybridized mouse cytotoxic T cell line which requires IL-2 for growth) were added and incubated for 24 hours; then tritiated thymidine was added and the cells incubated an additional 4 hours. The cells were then collected by centrifugation through oil and counted. Screening results were reported relative to the IL-1 standard run concurrently. Activity was considered to be >20% cell proliferation of the IL-1 standard as determined by thymidine uptake. Positive compounds that demonstrated reproducible biological activity were then tested for a dose response at $10^{-5}$, $3 \times 10^{-6}$, $4 \times 10^{-7}$M and $4 \times 10^{-8}$M. Compounds of the present invention were found to be active in the concentration range of $10^{-5}$M to $10^{-6}$M.

It should be understood by those skilled in the art that various modifications may be made in the present invention without departing from the spirit and scope thereof as described in the specification and defined in the appended claims.

What is claimed is:
1. A compound which is N-(1,1-dimethylethyl)-2-(2,4-bis(1,1-dimethylpropyl)phenoxy)-5-hydroxy-4-methylbenzamide
2. A pharmaceutical composition comprising N-(1,1-dimethylethyl)-2-(2,4-bis(1,1-dimethylpropyl)phenoxy-5-hydroxy-4-methylbenzamide, in a pharmaceutically acceptable carrier.

* * * * *